(12) United States Patent
Shinke et al.

(10) Patent No.: US 11,179,300 B2
(45) Date of Patent: Nov. 23, 2021

(54) EMULSION COSMETIC CONTAINING TITANIUM DIOXIDE POWDER (71) Applicant: SHISEIDO COMPANY, LTD., Tokyo (JP)

(72) Inventors: Mayo Shinke, Yokohama (JP); Shoko Ogawa, Yokohama (JP); Tomoko Ikeda, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 217 days.

(21) Appl. No.: 16/625,820

(22) PCT Filed: May 31, 2018

(86) PCT No.: PCT/JP2018/020907
§ 371 (c)(1),
(2) Date: Dec. 23, 2019

(87) PCT Pub. No.: WO2019/003790
PCT Pub. Date: Jan. 3, 2019

(65) Prior Publication Data
US 2020/0121569 A1    Apr. 23, 2020

(30) Foreign Application Priority Data

Jun. 26, 2017   (JP) .............................. JP2017-124672

(51) Int. Cl.
| A61K 8/06 | (2006.01) |
| A61K 8/25 | (2006.01) |
| A61K 8/29 | (2006.01) |
| A61K 8/41 | (2006.01) |
| A61K 8/894 | (2006.01) |
| A61K 8/895 | (2006.01) |
| A61Q 1/12 | (2006.01) |

(52) U.S. Cl.
CPC ............... *A61K 8/06* (2013.01); *A61K 8/25* (2013.01); *A61K 8/29* (2013.01); *A61K 8/416* (2013.01); *A61K 8/894* (2013.01); *A61K 8/895* (2013.01); *A61Q 1/12* (2013.01)

(58) Field of Classification Search
None
See application file for complete search history.

(56) References Cited

U.S. PATENT DOCUMENTS 7,175,835 B1 *  2/2007  Simoulidis ............... A61K 8/06
                                                424/400

FOREIGN PATENT DOCUMENTS

| JP | 4-364117 | 12/1992 |
| JP | 9-221411 | 8/1997 |
| JP | 10-182397 | 7/1998 |
| JP | 2000-191325 | 7/2000 |
| JP | 2003-192349 | 7/2003 |
| JP | 2006-265134 | 10/2006 |
| JP | 2010-173863 | 8/2010 |
| JP | 2011-068598 | 4/2011 |
| JP | 2013-227207 | 11/2013 |
| JP | 2014-084251 | 5/2014 |
| JP | 2016-037469 | 3/2016 |

OTHER PUBLICATIONS

PCT/JP2018/020907, ISR and Written Opinion dated Jul. 3, 2018, 15 pages—Japanese, 13 pages—English.

* cited by examiner

*Primary Examiner* — Nannette Holloman
(74) *Attorney, Agent, or Firm* — Andrew F. Young, Esq.; Nolte Lackenbach Siegel (57) ABSTRACT

An emulsion cosmetic maintains a concealing ability, allows light in a long wavelength region to transmit efficiently (i.e., an excellent red light selective transmit function), is spread easily, wherein a powder likeness cannot be felt upon use, and provides a natural finish when applied onto the skin. A titanium dioxide powder therefore is composed of particles having an apparent average particle diameter of 100 nm or more and less than 500 nm, an average crystallite diameter of 15 to 30 nm as measured by a X-ray diffraction method and a specific surface area of 10 to 30 m²/g, and each has a shape with radially projected needle-like projections are coagulated, and has a ratio of a longer axis to a shorter axis (i.e., a (longer axis)/(shorter axis) ratio) in the shape of 1.0 to 2.5. The emulsion cosmetic contains 0.1 to 25% by mass of the titanium dioxide powder, 0.1 to 5% by mass of disteardimonium hectorite and 0.1 to 8% by mass of a silicone surfactant.

7 Claims, 5 Drawing Sheets

FIG. 1

Apparent average particle size = (major axis + minor axis)/2

EMULSION COSMETIC CONTAINING TITANIUM DIOXIDE POWDER

CROSS REFERENCE TO RELATED APPLICATIONS

This application relates to and claims priority as a § 371 national phase, from PCT/JP2018/020907 filed May 31, 2018, the entire contents of which are incorporated herein by reference. This application also claims the priority of Japanese Patent Application No. 2017-124672, filed on Jun. 26, 2017, the disclosure of which is incorporated herein by reference in its entirety.

FIGURE SELECTED FOR PUBLICATION

FIG. 3

RELATED APPLICATION

This application claims the priority to Japanese Patent Application No. 2017-124672, filed on Jun. 26, 2017, the disclosure of which is incorporated herein by reference in its entirety.

FIELD OF THE INVENTION

The present invention relates to an emulsion cosmetic blended with a titanium dioxide powder, and particularly to an emulsion cosmetic which has an excellent function of transmitting more light in a long wavelength region (red-light selective transmission function) while concealing ability is maintained, can be spread lightly, is excellent in feeling in use (free of powdery feeling), and provides a natural makeup finish upon application to skin.

BACKGROUND OF THE INVENTION

Titanium dioxide has a high-refractive index and excellent whiteness, concealing ability, and coloring ability, and has therefore been widely used as a white pigment for such as paints and plastics. Furthermore, titanium dioxide can also be used for cosmetics and catalysts as a substance for shielding (blocking) ultraviolet lights such as ultraviolet light absorbers or ultraviolet light shielding agents by controlling the particle size or photoactivity thereof. For that reason, in recent years, research and development has been actively conducted on such use of titanium dioxide.

It has been known that when a titanium dioxide powder having an apparent specific average particle size, which is formed of small spherical particles of a titanium dioxide having a specific average primary particle size and a spherical moss-like shape made up of a large number of titanium dioxide, is used for cosmetics, the titanium dioxide powder serves as a functional material capable of imparting a good slipperiness and excellent light resistance that conventional titanium dioxides do not have (Patent Literature 1).

Further, a cosmetic for lips comprising 1 to 15% by mass of rutile titanium dioxide aggregated particles having an average particle size of 0.2 to 0.4 μm and an average coefficient of friction (MIU value) of 0.4 to 0.6, and 1 to 40% by mass of semisolid oil has been known to give gloss, suppress noticeableness of wrinkles of lips, and provide excellent long-lasting makeup properties (Patent Literature 2).

Moreover, it has been known that a cosmetic containing a coloring material having a small absorbance of light on a long wavelength side (wavelength of 630 to 700 nm) in a visible light region makes a light transmitting property inside of skin close to bare skin, and thus a natural makeup finish can be achieved (Patent Literature 3).

As described above, as the titanium dioxide having an improved light transmittance for light on the long wavelength side, a rutile titanium dioxide in form of thin strips or straw bundles has been developed. It has a particulate form of which rod-shaped particles are orientated and aggregated in bundles, and an apparent average length of the orientated and aggregated particle is 80 to 300 nm, an apparent average width of the orientated and aggregated particle is 30 to 150 nm, an apparent average axial ratio represented by the apparent average length/the apparent average width is 1.1 to 4, and a specific surface area is 120 to 180 $m^2/g$. This titanium dioxide has been known to have a high-level of transparency and ultraviolet light shielding ability (Patent Literature 4).

However, because this titanium dioxide is an aggregate of rod-shaped particles and has many voids in the secondary aggregate, the titanium dioxide has a lowered apparent refractive index and thus the concealing ability is insufficient when it is actually added to cosmetics. Furthermore, because the titanium dioxide is intended mainly for ultraviolet protection, the secondary aggregate has an apparent particle size of less than 100 nm that is clearly smaller than the particle size capable of maximizing the scattering effect of the titanium dioxide based on Mie theory, and this is also a factor making the concealing ability low.

From such circumstances, development in an emulsion cosmetic blended with titanium dioxide that provides natural finish upon application to skin is desired.

CITATION LIST

Patent Literatures

Patent Literature 1: Japanese Unexamined Patent Publication No. 2000-191325 A

Patent Literature 2: Japanese Unexamined Patent Publication No. 2010-24189 A

Patent Literature 3: Japanese Unexamined Patent Publication No. 2006-265134 A

Patent Literature 4: Japanese Unexamined Patent Publication No. 2010-173863 A

DISCLOSURE OF THE INVENTION

Problem to be Solved by the Invention

The present invention has been made in view of the above-mentioned conventional art, and an object to be solved is to provide an emulsion cosmetic which has an excellent function of transmitting more light in a long wavelength region (red-light selective transmission function) while concealing ability is maintained, is excellent in feeling in use, and provides a natural makeup finish upon application to skin.

Means to Solve the Problem

The present inventors have diligently investigated on the above-mentioned problem and as a result, it is found that titanium dioxide obtained by calcining a specific titanium dioxide to have a specific particle size, a specific crystallite size and a specific surface area shows an excellent red-light selective transmission function while having a sufficient concealing ability required for cosmetics.

Moreover, it is found that an emulsion cosmetic blended with said titanium dioxide can be spread lightly, is excellent in feeling in use (free of powdery feeling), and provides a natural makeup finish upon application to skin.

That is, an emulsion cosmetic of the present invention, comprises:

0.1 to 25% by mass of a titanium dioxide powder having an apparent average particle size of 100 nm or more and less than 500 nm, an average crystallite size measured by X-ray diffractometry of 15 to 30 nm, and a specific surface area of 10 to 30 m$^2$/g, the titanium dioxide powder having a shape in which needle-shaped projections that projects out radially are coagulated, and a ratio between a minor axis and a major axis (major axis/minor axis) of 1.0 or more and less than 2.5;

0.1 to 5% by mass of disteardimonium hectorite; and
0.1 to 8% by mass of a silicone surfactant.

Furthermore, an emulsion cosmetic according to the present invention comprises:

0.1 to 25% by mass of a rutile titanium dioxide powder having an average crystallite size measured by X-ray diffractometry of 15 to 30 nm, a specific surface area of 10 to 30 m$^2$/g, a reflectance at 450 nm of 1.3 times or more than the reflectance at 650 nm, and a color difference ($\Delta E$) of 22 or less;

0.1 to 5% by mass of disteardimonium hectorite; and
0.1 to 8% by mass of a silicone surfactant.

With respect to the color difference ($\Delta E$), the titanium dioxide powder was dispersed and mixed to a nitrocellulose lacquer in a concentration of 5%, and the obtained dispersion was applied to a black-and-white concealing ability test chart, JIS-K5400, at a coating thickness of 0.101 μm and dried to prepare a test sample. Using the prepared test sample, a colorimetric measurement was performed on each coating surface of a black portion and a white portion of the chart with a spectrocolorimeter. The color difference ($\Delta E$) was calculated based on Hunter Lab color space.

Furthermore, an emulsion cosmetic according to the present invention, comprises:

0.1 to 25% by mass of a titanium dioxide powder which is a rutile titanium dioxide powder obtained by calcining a rutile titanium dioxide having needle-shaped projections on the particle surface where needle-shaped particles are radially orientated and aggregated and satisfying the following (a) to (c), the titanium dioxide powder having an apparent average particle size of 100 nm or more and less than 500 nm, an average crystallite size measured by X-ray diffractometry is 15 to 30 nm, and a specific surface area of 10 to 30 m$^2$/g;

0.1 to 5% by mass of disteardimonium hectorite; and
0.1 to 8% by mass of a silicone surfactant.

(a) An apparent average particle size is 100 nm or more and less than 500 nm
(b) An average crystallite size measured by X-ray diffractometry is 1 to 25 nm
(c) A specific surface area is 40 to 200 m$^2$/g Furthermore, the emulsion cosmetic according to the present invention comprises:

0.1 to 25% by mass of a titanium dioxide powder which is a rutile titanium dioxide powder obtained by calcining a rutile titanium dioxide having needle-shaped projections on the particle surface and satisfying the following (a) to (c), the titanium dioxide powder in which a specific surface area of the rutile titanium dioxide powder after the calcination is 8 to 50% with respect to that of before the calcination;

0.1 to 5% by mass of disteardimonium hectorite; and
0.1 to 8% by mass of a silicone surfactant.

(a) An apparent average particle size is 100 nm or more and less than 500 nm
(b) An average crystallite size measured by X-ray diffractometry is 1 to 25 nm
(c) A specific surface area is 40 to 200 m$^2$/g In the emulsion cosmetic, the calcination temperature of the titanium dioxide is preferably 500 to 800° C.

In the emulsion cosmetic, the calcination temperature of the titanium dioxide is preferably 550 to 750° C.

In the emulsion cosmetic, the reflectance at 450 nm is preferably 1.3 times or more of the reflectance at 650 nm, and preferably transmits more light on a long wavelength side.

Effect of the Invention

According to the present invention, an emulsion cosmetic which has an excellent function of transmitting more light in a long wavelength region (red-light selective transmission function) while concealing ability is maintained, can be spread lightly, is excellent in feeling in use (free of powdery feeling), and provides a natural makeup finish upon application to skin can be provided.

MODE FOR CARRYING OUT THE INVENTION

The titanium dioxide powder according to the present invention is a titanium dioxide powder obtained by calcining titanium dioxide having needle-shaped projections on the particle surface where needle-shaped particles are radially orientated and aggregated at 500 to 800° C., and more preferably at 550 to 750° C. The titanium dioxide powder has an average crystallite size measured by X-ray diffractometry of 15 to 30 nm; an apparent average particle size of titanium dioxide is 100 nm or greater and less than 500 nm, and more preferably 200 to 400 nm; and a specific surface area is 10 to 30 m$^2$/g.

<Titanium Dioxide Used as a Mother Nucleus>

The crystalline forms of titanium dioxide used as a mother nucleus include anatase and rutile by crystal structure. The crystalline form of titanium dioxide used in the present invention needs to be rutile which has a high concealing ability since it is low in photocatalytic activity and high in refractive index.

As a rutile titanium dioxide used as a mother nucleus, the titanium dioxide having a function of transmitting red light is used. Considering that a shrinkage phenomenon usually takes place after the calcination, an apparent average particle size of the titanium dioxide used as a mother nucleus is desired to be 100 nm or more and less than 500 nm, and more preferably 200 to 400 nm in terms of achieving the concealing ability by light scattering and the excellent function of transmitting red-light of the titanium dioxide obtained in the present invention.

The rutile titanium dioxide used as a mother nucleus may be in a shape of cocoon, straw bundle, strip, sphere, needle, rod or the like. In the present invention, it is preferable to have needle-shaped projections on the particle surface where rod-shaped or needle-shaped particles are radially orientated and aggregated.

The specific surface area of the titanium dioxide used as a mother nucleus is preferably 40 to 200 $m^2/g$ in terms of improving an apparent refractive index efficiently by calcination.

The rutile titanium dioxide used as a mother nucleus preferably has an average crystalline size measured by X-ray diffractometry of 1 to 25 nm.

The rutile titanium dioxide used as a mother nucleus may be commercially available products. Examples thereof include ST-700 series manufactured by Titan Kogyo, Ltd. Among the ST-700 series, ST-710 may be used.

<Titanium Dioxide Powder Used in the Present Invention>

The titanium dioxide powder of the present invention can be obtained by calcining titanium dioxide used as a mother nucleus.

A calcination temperature depends on a device that performs calcination. However, it is desired that a temperature condition is set so that: voids which are present between the needle-shaped particles, in which needle-shaped projections that exist before the calcination and radially project out from the particle surface, due to coagulation by calcination are reduced; and an average crystallite size measured by X-ray diffractometry is not increased excessively due to sintering of the needle-shaped particles. Such a temperature condition allows both the concealing ability and the red-light selective transmission function to be achieved sufficiently.

The titanium dioxide powder used in the present invention is in form of particles in which needle-shaped projections that exist before the calcination and radially project out from the particle surface are coagulated by calcining. A ratio between a minor axis and a major axis of the particle (major axis/minor axis) is 1.0 or more and less than 2.5, and more preferably 1.0 to 2.0.

A suitable calcination temperature varies depending on the calcination device. When the calcination is performed in a muffle furnace or a rotary kiln which is a commonly-used calcination furnace, it is desired that the calcination is performed at a temperature of 500 to 800° C., and more preferably 550 to 750° C. When the temperature is below 500° C., the concealing ability is insufficient since voids that exist before the calcination are not sufficiently reduced. When the temperature exceeds 800° C., the red-light selective transmission function is lost since the sintering proceeds excessively.

The titanium dioxide of the present invention needs to have the average crystallite size measured by X-ray diffractometry of 15 to 30 nm.

When the crystallite size is less than 15 nm, it is not preferable because the sufficient concealing ability cannot be obtained. Additionally, when the crystallite size is more than 30 nm, it is not preferable because the sufficient red-light selective transmission function is lost as the sintering proceeds.

Further, the titanium dioxide powder of the present invention needs to have the apparent average particle size of 100 nm or more and less than 500 nm, and more preferably 200 to 400 nm, in terms of efficiently achieving the concealing ability due to light scattering and excellence in the red light transmission function.

The specific surface area of the titanium dioxide powder used in the present invention is an index that shows a reduction in voidage and a progression of the sintering of the obtained titanium dioxide particles. The specific surface area after the calcination of the titanium dioxide powder used as a mother nucleus is preferably within a range of 8 to 50%, and more preferably 8 to 30% compared to before the calcination (100%).

Furthermore, the specific surface area of the titanium dioxide powder of the present invention needs to be 10 to 30 $m^2/g$. The specific surface area of less than 10 $m^2/g$ is not preferable because the sintering proceeds and thus the sufficient red-light selective transmission function is lost. Additionally, the specific surface area of more than 30 $m^2/g$ is not preferable because the sufficient concealing ability cannot be achieved due to the existence of too many voids.

The titanium dioxide powder of the present invention can be surface treated after the calcination. Performing surface treatment can improve long-lasting makeup properties involving viscosity, dispersibility to oil, and water repellency, and at the same time, produce a titanium dioxide that is excellent in usability.

Examples of inorganic substances which can be used as a surface treatment agent include a hydrous oxide or oxide of metals such as aluminum, silicon, zinc, titanium, zirconium, iron, cerium, and tin. The metallic salt to be used is not limited in particular.

Examples of an organic substance, which can be used as a surface treatment agent after surface treatment with metal oxide or hydroxide such as aluminum hydroxide or oxide and is intended to impart a lipophilic property, include fatty acids such as stearic acid, oleic acid, isostearic acid, myristic acid, palmitic acid, and behenic acid, silicone compounds such as methylhydrogenpolysiloxane, dimethicone, alkyl (C8-C18 or the like)trialkoxysilane, amino-modified silicone, and carboxyl-modified silicone, fluorine compounds such as perfluoroalkyl alkyl phosphate, dextrin myristate, dextrin palmitate, and amino acid derivatives such as lauroyl lysine, lauroyl glutaminate, or the like.

It is preferable that these surface treatment agents are 1 to 10% by mass with respect to the titanium dioxide powder since the concealing ability is high.

The titanium dioxide powder used in the present invention can be widely blended in cosmetics, pigments, inks, and paints.

The blending amount of titanium dioxide used in the present invention is 0.1 to 25% by mass, and more preferably 5 to 15% by mass with respect to the total weight of a solid powder cosmetic. When the blending amount is less than 0.1% by mass, the effect achieved by the blending of titanium dioxide of the present invention may not be achieved. When the blending amount exceeds 25% by mass, the makeup finish may be unnatural.

The emulsion cosmetic according to the present invention uses: (A) disteardimonium hectorite; and (B) a silicone surfactant. Each of them will be described in detail hereinbelow.

<(A) Disteardimonium Hectorite>

In the present invention, an oil phase of the cosmetic is thickened or solidified by disteardimonium hectorite (A).

The disteardimonium hectorite (A) in the present invention is one kind of an organic modified clay mineral conventionally used as oil phase thickeners (gelling agents) in cosmetics. For example, disteardimonium hectorite commercially sold as "BENTONE 38V" or "BENTONE 38VCG" can be used preferably.

The blending amount of disteardimonium hectorite in the emulsion cosmetic of the present invention is 0.1 to 5% by mass, preferably 0.1 to 4% by mass, and more preferably 0.1 to 3% by mass. When the blending amount is too small, stability upon storage may not be maintained or fitting feeling may not be achieved. When the blending amount is too large, spreading may become heavier or powdery feeling may be felt.

<(B) Silicone Surfactant>

The component (B) of the present invention is one or two kinds of a silicone surfactant modified by a polyether group or a polyglycerin group.

Examples of silicone surfactants modified by a polyether group include, but not limited to: PEG-11 methyl ether dimethicone, PEG-10 dimethicone, PEG-9 polydimethylsiloxyethyl dimethicone, lauryl PEG-9 polydimethylsiloxyethyl dimethicone, and cetyl PEG/PPG-10/1 dimethicone. Commercially available products thereof are KF-6011, KF-6043, KF-6017, KF-6017P, KF-6028, KF-6028P, KF-6038 and KF-6048 (all manufactured by Shin-Etsu Chemical Co., Ltd.). Examples of silicone surfactants modified by a polyglycerin group include, but not limited to: polyglyceryl-3 disiloxane dimethicone, polyglyceryl-3 polydimethylsiloxyethyl dimethicone, and lauryl polyglyceryl-3 polydimethylsiloxyethyl dimethicone. Commercially available products thereof are KF-6100, KF-6104, KH-6106 and KF-6105 (all manufactured by Shin-Etsu Chemical Co., Ltd.). As the component (B), the above surfactants may be used alone, or in combination of two or more.

Furthermore, a partially crosslinked polyether modified silicone or a partially crosslinked polyglycerin modified silicone can be used as the component (B). The component (B) may be only the partially crosslinked polyether modified silicone or the partially crosslinked polyglycerin modified silicone. The partially crosslinked polyether modified silicone is a three-dimensionally crosslinked substance of which an organopolysiloxane chain is crosslinked by a polyether residue. The partially crosslinked polyglycerin modified silicone is a three-dimensionally crosslinked substance of which an organopolysiloxane chain is crosslinked by a polyglycerin residue. Examples thereof include, but not limited to: dimethicone/PEG-10/15 crosspolymer, PEG-15/lauryl dimethicone crosspolymer, PEG-15/lauryl polydimethylsiloxyethyl dimethicone crosspolymer, dimethicone/polyglycerin-3 crosspolymer, lauryl dimethicone/polyglycerin-3 crosspolymer, and polyglyceryl-3/lauryl polydimethylsiloxyethyl dimethicone crosspolymer. They are commercially sold as a swelling substance that contains a silicone oil or other oils. Examples thereof include, but not limited to: KSG-210, 240, 310, 340, 320Z, 360Z, KSG-710, 810, and 820Z (all manufactured by Shin-Etsu Chemical Co., Ltd.).

The blending amount of the component (B) is 0.1 to 8% by mass, preferably 0.1 to 7% by mass, and more preferably 0.1 to 6% by mass with respect to the mass of the cosmetic in total. When the blending amount is too small, it becomes difficult for the cosmetic to be obtained to have a sufficient stability upon storage. When the blending amount is too large, the cosmetic may be sticky.

The present invention can comprise other optional surfactants other than the silicone surfactant (B). Examples of the other surfactant include, but not limited to, fatty acid glyceryl ester.

It is preferable to blend 0.1 to 10% by mass of an elastic powder (C) to the present invention. By blending the component (C), pores become more difficult to be noticed while natural makeup finish and natural redness is maintained.

It is preferable to blend 0.1 to 10% by mass of a hydrophobized fine-particle titanium dioxide (D) (specific surface area of 30 to 70 $m^2/g$) to the present invention. By blending the component (D), spots and freckles can be covered more while natural finish and natural redness is maintained.

<Oily Component>

Oily components that are usually used in cosmetics can be used within the range of not inhibiting the stability of the emulsion.

Silicone oils may be used as a liquid oily component. Examples of the silicone oil include, but not limited to: chained silicone oils such as dimethylpolysiloxane, methylphenylpolysiloxane, and methyl hydrogen polysiloxane; and cyclic silicone oils such as octamethylcyclotetrasiloxane, decamethylcyclopentasiloxane, and dodecamethylcyclohexasiloxane.

Examples of polar oils include, but not limited to, ester oils such as cetyl octanoate, hexyl laurate, isopropyl myristate, octyl palmitate, isocetyl stearate, isopropyl isostearate, octyl isopalmitate, isodecyl isostearate, 2-ethylhexyl succinate, and diethyl sebacate.

Examples of non-polar oils include, but not limited to, hydrocarbon oils such as liquid paraffin, squalane, squalene, and paraffin.

Solid oils can be further comprised as the oily component. Examples of solid oils include, but not limited to: solid fats such as cacao butter, coconut oil, horse oil, hydrogenated coconut oil, palm oil, beef tallow, sheep tallow, and hydrogenated caster oil; hydrocarbons such as paraffin wax (linear hydrocarbon), microcrystalline wax (branched saturated hydrocarbon), ceresin wax, Japan wax, montan wax, and Fischer-Tropsch wax; waxes such as beeswax, lanolin, carnauba wax, candelilla wax, rice bran wax (rice wax), spermaceti, jojoba oil, bran wax, montan wax, kapok wax, bayberry wax, shellac wax, sugarcane wax, lanolin fatty acid isopropyl ester, hexyl laurate, reduced lanolin, hardened lanolin, POE lanolin alcohol ether, POE lanolin alcohol acetate, POE cholesterol ether, lanolin fatty acid polyethylene glycol, and POE hydrogenated lanolin alcohol ether; higher fatty acids such as myristic acid, palmitic acid, stearic acid, and behenic acid; and higher alcohols such as cetyl alcohol, stearyl alcohol, behenyl alcohol, myristyl alcohol, and cetostearyl alcohol.

<Aqueous Component>

Aqueous components such as water that are usually used in cosmetics can be blended within the range of not inhibiting the stability of the emulsion.

Examples of moisturizers include, but not limited to, 1,3-butylene glycol, polyethylene glycol, propylene glycol, dipropylene glycol, hexylene glycol, glycerin, diglycerin, xylitol, maltitol, maltose, and D-mannitol.

Examples of water-soluble polymers include, but not limited to: plant based polymers such as gum Arabic, carrageenan, pectine, agar, quince seed (cydonia oblonga), starch, and algae colloid (brown algae extract); microorganism based polymers such as dextran, and pullulan; animal based polymers such as collagen, casein, and gellatin; starch based polymers such as carboxymethyl starch, and methyl hydroxypropyl starch; alginic acid based polymers such as sodium alginate; vinyl based polemers such as carboxyvinyl polymer (CARBOPOL, etc.); polyoxyethylene based polymers; polyoxyethylene polyoxypropylene copolymer based polymers; acrylic polymers such as sodium polyacrylate, and polyacrylamide; and inorganic water-soluble polymers such as bentonite, magnesium aluminum silicate, and laponite.

Examples of sequestrants include, but not limited to, edetic acid sodium salt, sodium metaphosphate, and phosphoric acid.

Examples of anti-oxidants include, but not limited to, ascorbic acid, α-tocopherol, dibutylhydroxytoluene, and butylhydroxyanisol.

Examples of drugs include, but not limited to: vitamins such as vitamin A oil, retinol, retinol palmitate, inositol, pyridoxine hydrochloride, benzyl nicotinate, nicotinic acid amide, dl-α-tocopherol nicotinate, magnesium ascorbyl phosphate, ascorbic acid-2-glucoside, vitamin D2 (ergocalciferol), L-ascorbic acid dl-α-tocopherol phosphoric acid diester potassium salt, dl-α-tocopherol, dl-α-tocopherol acetate, pantothenic acid, and biotin; anti-inflammatory agents such as allantoin, and azulene; whitening agents such as arbutin; astringents such as zinc oxide, and tannic acid; sulphur; lysozyme chloride; pyridoxine hydrochloride; and γ-oryzanol.

The above-mentioned drugs can be used in a released state. Those that can form salts can be used in forms of salts of acids or bases, and those that have carboxylic acid groups can be used in form of esters thereof.

[Other Components]

The emulsion cosmetic composition according to the present invention may include, as appropriate and as necessary, other components within the range of not inhibiting the effect of the present invention such as esters, water-soluble polymers, thickeners, film-forming agents, ultraviolet light absorbers, lower alcohols, polyhydric alcohols, saccharides, amino acids, organic amines, polymer emulsions, pH adjusters, skin nutrients, vitamins, antioxidants, perfumes and the like, and can be produced by a usual method in accordance with the aimed dosage forms.

Specific components that can be blended are listed below. The emulsion cosmetic can be prepared by blending the above-mentioned essential components and one or two or more of the optional components below.

Examples of natural water-soluble polymers include, but not limited to, plant based polymers (such as gum Arabic, gum tragacanth, galactan, guar gum, locust bean gum, gum karaya, carrageenan, pectine, agar, quince seed (cydonia oblonga), algae colloid (brown algae extract), starch (rice, corn, potato, wheat), glicyrrhizic acid); microorganism based polymers (such as xanthan gum, dextran, succinoglycan, pullulan, etc), and animal based polymers (such as collagen, casein, albumin, gelatin, etc).

Examples of the semisynthetic water-soluble polymer include, but not limited to, starch based polymers (such as carboxymethyl starch, methylhydroxypropyl starch, etc); cellulose based polymers (such as methylcellulose, ethylcellulose, methylhydroxypropylcellulose, hydroxyethylcellulose, cellulose sodium sulfate, hydroxypropylcellulose, carboxymethylcellulose, sodium carboxymethyl cellulose, crystalline cellulose, cellulose powder, etc); and algin acid based polymers (such as sodium alginate, propylene glycol alginate ester, etc).

Examples of synthetic water-soluble polymers include, but not limited to, vinyl based polymers (such as polyvinyl alcohol, polyvinyl methyl ether, polyvinylpyrrolidone, carboxyvinylpolymer, etc); polyoxyethylene based polymers (such as polyoxyethylenepolyoxypropylene copolymer such as polyethylene glycol 20,000, 40,000 and 60,000, etc); acrylic polymers (such as sodium polyacrylate, polyethylacrylate, polyacrylamide, etc); polyethyleneimine; and cationic polymers.

Examples of thickeners include, but not limited to, gum Arabic, carrageenan, karaya gum, gum tragacanth, carob gum, quince seed (cydonia oblonga), casein, dextrin, gelatin, sodium pectate, sodium alginate, methylcellulose, ethyl cellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyldimethylammonium sulfate cellulose, xanthan gum, magnesium aluminum silicate, bentonite, hectorite, magnesium aluminum silicate (veegum), laponite, and silicic anhydride.

Examples of ultraviolet light absorbers include, but not limited to, benzoic acid family ultraviolet light absorbers (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc); anthranilic acid family ultraviolet light absorbers (such as homomenthyl N-acetylanthranilate etc); salicylic acid family ultraviolet light absorbers (such as amyl salicylate, menthyl salicylate, homomenthyl salicylate, octyl salicylate, phenyl salicylate, benzyl salicylate, p-isopropanolphenyl salicylate, etc); cinnamic acid family ultraviolet light absorbers (such as octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxy cinnamate, etc); benzophenone family ultraviolet light absorbers (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc); 3-(4'-methylbenzylidene)-d,l-camphor and 3-benzylidene-d,l-camphor; 2-phenyl-5-methylbenzoxazol; 2,2'-hydroxy-5-methylphenylbenzotriazol, 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; dimorpholinopyridazinone; 2-ethylhexyl 2-cyano-3,3-diphenylacrylate; and 2,4-bis-{[4-(2-ethylhexyloxy)-2-hydroxy]-phenyl}-6-(4-methoxyphenyl)-(1,3,5)-triazine.

Examples of lower alcohols include, but not limited to, ethanol, propanol, isopropanol, isobutyl alcohol, and t-butyl alcohol.

Examples of polyhydric alcohols include, but not limited to: dihydric alcohol (such as ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc); trihydric alcohol (such as glycerin, trimethylolpropane, etc); tetrahydric alcohol (such as such as pentaerythritol such as 1,2,6-hexanetriol, etc); pentahydric alcohol (such as xylitol, etc); hexahydric alcohol (such as sorbitol, mannitol, etc); polyhydric alcohol polymer (such as diethylene glycol, dipropylene glycol, triethylene glycol, polypropylene glycol, tetraethylene glycol, diglycerin, polyethylene glycol, triglycerin, tetraglycerin, polyglycerin, etc); dihydric alcohol alkyl ethers (such as ethylene glycol monomethyl ether, ethylene glycol monoethyl ether, ethylene glycol monobutyl ether, ethylene glycol monomphenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, etc); dihydric alcohol alkyl ethers (such as diethylene glycol monomethyl ether, diethylene glycol monoethyl ether, diethylene glycol monombutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc); dihydric alcohol ether ethers (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc); glycerin monoalkyl ether (such as chimyl alcohol, selachyl alcohol, batyl alcohol, etc); sugar alcohol (such as sorbitol, maltitol, maltotriose, mannitol, sucrose, erythritol, glucose, fructose, starch sugar, maltose, xylitose, starch sugar hydrogenated alcohol, etc); glycolide, tetrahydrofurfuryl alcohol; POE-tetrahydrofurfuryl alcohol; POP/POE-butyl ether; tripolyoxypropylene glycerin ether; POP-glycerin ether; POP-glycerin ether phosphoric acid; POP/POE-pentaerythritol ether; and polyglycerin.

Examples of monosaccharides include, but not limited to: triose (such as D-glyceryl aldehyde, dihydroxyacetone, etc); tetrose (such as D-erythrose, D-erythrulose, D-threose, erythritol, etc); pentaose (such as L-arabinose, D-xylose, L-lyxose, D-arabinose, D-ribose, D-ribulose, D-xylulose, L-xylulose, etc); hexalose (such as D-glucose, D-talose, D-psicose, D-galactose, D-fructose, L-galactose, L-mannose, D-tagatose, etc); heptose (such as aldoheptose, heptose); octose (such as octulose, etc); deoxy sugar (such as 2-deoxy-D-ribose, 6-deoxy-L-galactose, 6-deoxy-L-mannose, etc); amino sugar (such as D-glucosamine, D-galactosamine, sialic acid, amino uronic acid, muramic acid, etc); and uronic acid (such as D-grucuronic acid, D-mannuronic acid, L-guluronic acid, D-garacturonic acid, L-iduronic acid, etc).

Examples of oligosaccharides include, but not limited to, sucrose, guntianose, umbelliferose, lactose, planteose, isolignoses, α,α-trehalose, raffinose, lignoses, umbilicin, stachyose, and verbascoses.

Examples of polysaccharides include, but not limited to: cellulose, quince seed, chondroitinsulfate, starch, galactan, dermatan sulfate, glycogen, gum Arabic, heparansulfate, hyaluronan, gum tragacanth, keratan sulfate, chondoroitin, xanthan gum, mucoitin sulfate, guar gum, dextran, keratosulfate, locust bean gum, succinoglycan, and caronic acid.

Examples of amino acids include, but not limited to: neutral amino acid (such as threonine, cysteine, etc); and basic amino acid (such as hydroxylysine, etc). Examples of amino acid derivatives include, but not limited to, sodium acyl sarcosinate (sodium lauroyl sarcosinate), acyl glutamate, sodium acyl β-alanine, glutathione, and pyrrolidone carboxylate.

Examples of organic amines include, but not limited to, monoethanolamine, diethanolamine, triethanolamine, morpholine, triisopropanolamine, 2-amino-2-methyl-1,3-propanediol, and 2-amino-2-methyl-1-propanol.

Examples of polymer emulsions include, but not limited to, acrylic resin emulsion, ethyl polyacrylate emulsion, acrylic resin solution, polyacrylalkylester emulsion, polyvinyl acetate resin emulsion, and natural rubber latex.

Examples of pH adjusters include, but not limited to, buffers such as lactic acid-sodium lactate, citric acid-sodium citrate, and succinic acid-sodium succinate.

Examples of vitamins include, but not limited to, vitamine A, B1, B2, B6, C, E and derivatives thereof, pantothenic acid and derivatives thereof, and biotin, Examples of anti-oxidant aids include, but not limited to, phosphoric acid, citric acid, ascorbic acid, maleic acid, malonic acid, succinic acid, fumaric acid, cephalin, hexamethaphosphate, phytic acid, and ethylenediaminetetraacetate.

Examples of other blendable compositions include, but not limited to: antiseptic agents (such as ethylparaben, butylparaben, chlorphenesin, 2-phenoxyethanol, etc); antiphlogistics (such as glycyrrhizinic acid derivatives, glycyrrhetic acid derivatives, salicylic acid derivatives, hinokitiol, zinc oxide, allantoin, etc); skin-whitening agents (such as placental extract, saxifrage extract, arbutin, etc); various extracts (such as phellodendron bark (cork tree bark), coptis rhizome, lithospermum, peony, swertia herb, birch, sage, loquat, carrot, aloe, mallow, iris, grape, coix seed, sponge gourd, lily, saffron, cnidium rhizome, ginger, hypericum, restharrow, garlic, red pepper, citrus unshiu, Japanese angelica, seaweed, etc); activators (such as royal jelly, photosenstizer, cholesterol derivatives, etc); blood circulation promotors (such as nonylic acid vanillylamide, nicotine acid benzyl ester, nicotine acid β-butoxyethyl ester, capsaicin, zingerone, cantharides tincture, ichthammol, tannic acid, α-bomeol, tocopheryl nicotinate, meso-inositol hexanicotinate, cyclandelate, cinnarizine, tolazoline, acetylcholine, verapamil, cepharanthine, γ-oryzanol, etc); antiseborrheric agents, (such as sulfur, thianthl, etc); and anti-inflammatory agents (such as tranexamic acid, thiotaurine, hypotaurine, etc).

Furthermore, sequestrants such as disodium edetate, trisodium edetate, sodium citrate, sodium polyphosphate, sodium metaphosphate, gluconic acid, malic acid, and the like; various crude drug extracts such as cafein, tannin, verapamil, tranexamic acid and derivatives thereof, licorice, Chinese quince, Pyrola japonica and the like; drugs such as tocopherol acetate, glycyrrhetinic acid, glycyrrhizic acid and derivatives thereof, or salts thereof; skin-whitening agents such as vitamin C, magnesium ascorbyl phosphate, ascorbic acid glucoside, arbutin, kojic acid and the like; amino acids such as arginine and lysine and the like and derivatives thereof; and saccharides such as fructose, mannose, erythritol, trehalose, xylitol, and the like can also be blended.

Examples of the emulsion cosmetics according to the present invention include products such as skin-whitening beauty essences, milky lotions, creams, face masks, makeup bases, BB creams, sunscreens, foundations, lip sticks, eye shadows, eye liners, mascaras, face washes, sprays, mousses, hair treatments, shampoos, and the like.

In the present invention, forms of containers are not limited in particular. For example, it is possible to impregnate this cosmetic to an impregnating body to store it inside a hermetic compact container. Examples of the impregnating body include, but not limited to: resins; pulp; non-woven fabrics made of cotton and the like, or of mixed materials; resin-treated fiber bodies; foams such as sponges; and porous bodies having continuous pores. Examples of materials of the impregnating bodies include: NBR (acrylonitrile butadiene rubber), SBR (styrene butadiene rubber), NR (natural rubber), urethane, nylon, polyolefin, polyester, EVA (ethylene vinyl acetate), PVA (polyvinyl alcohol), silicone, and elastomer, but it is not limited in particular as long as the impregnating body can contain the cosmetic

[Production Method of the Emulsion Cosmetic According to the Present Invention]

The emulsion cosmetic according to the present invention is produced by mixing and dispersing a powder to an oil phase, and then adding an aqueous phase to be mixed.

EXAMPLES

The present invention will be described with reference to the following examples. However, the present invention is not limited to the following examples. The unit of the blending amount is "% by mass" with respect to the system to which the component is to be blended unless otherwise specified.

Before describing Examples, evaluation method of the test of titanium dioxide used in the present invention is described.

Evaluation (1): Method for Measuring Average Crystallite Size

A sample was measured by an X-ray diffractometery (Geigerflex, manufactured by Rigaku Corporation). The average crystallite size was calculated by Scherrer's equation.

Evaluation (2): Evaluation of Concealing Ability

A titanium dioxide powder was dispersed and mixed into a nitrocellulose lacquer in a concentration of 5%. A resultant dispersion was applied to a black-and-white concealing ability test chart in accordance with JIS-K5400 with a coating thickness of 0.101 μm and dried to prepare a test sample. Using the prepared test sample, a colorimetric measurement was performed on each coating surface of a black portion and a white portion of the chart with a spectrocolorimeter (CM-2600, manufactured by Konica Minolta, Inc.). A color difference (ΔE) was calculated based on Hunter Lab color space and evaluated it as the concealing ability. Note that the higher the ΔE, the lower the concealing ability; and the lower the ΔE, the higher the concealing ability.

$$\Delta E = \sqrt{(L1-L2)^2 + (a1-a2)^2 + (b1-b2)^2}$$

(Evaluation criteria)
A: ΔE≤22
B: 22<ΔE≤25
C: 25<ΔE

Evaluation (3): Evaluation of Red-Color Transmitting Property

Among spectral reflectances at each wavelengths measured on the black portion of the chart, similar to the concealing ability described above, the reflectances at wavelengths of 450 nm and 650 nm were used to calculate their ratio, (reflectance at a wavelength of 450 nm/reflectance at 650 nm: R450/R650). The ratio represents a red-color transmitting property.

Note that the higher the R450/R650, the higher the red-color transmitting property; and the lower R450/R650, the lower the red-color transmitting property.

(Evaluation criteria)
A: 1.4<R450/R650
B: 1.35<R450/R650≤1.4
C: 1.3<R450/R650≤1.35
D: R450/R650≤1.3

Evaluation (4): Method for Measuring Specific Surface Area

The specific surface area per unit mass can be determined by a nitrogen adsorption method known as the BET (Brunauer-Emmett-Teller) method described in The Journal of the American Chemical Society, vol. 60, p. 309, February 1938 which corresponds to the ISO international standard 5794-1 (Appendix D)

Evaluation (5): Method for Measuring Apparent Average Particle Size.

Figure 1:
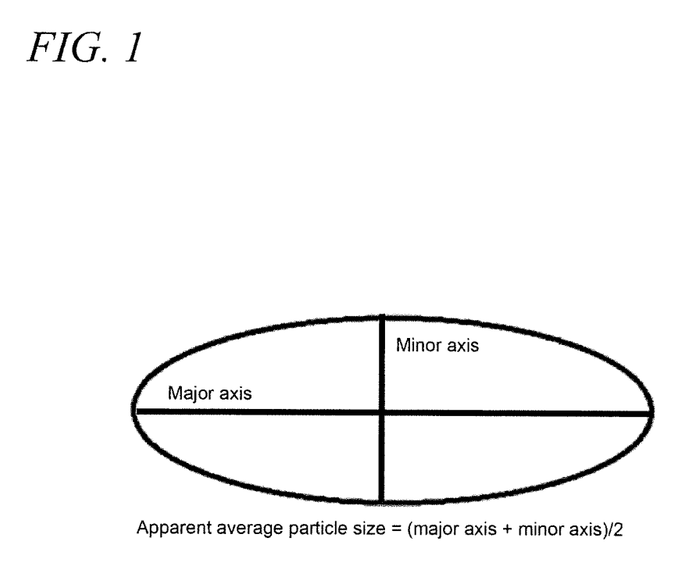
FIG. 1 shows a method for measuring an apparent average particle size.

The method shown in FIG. 1 is used to calculate an average value of the lengths of the major axis and the minor axis of the particle.

[Selection of Titanium Dioxide Used as a Mother Nucleus]

First of all, the present inventors used commercially available pigment grade rutile and anatase titanium oxides and evaluated them by the above evaluation methods. The results are shown in Table 1.

TABLE 1

| | Test Example | |
|---|---|---|
| | 1<br>Pigment grade<br>titanium dioxide<br>(rutile) *1 | 2<br>Pigment grade<br>titanium dioxide<br>(anatase) *2 |
| Concealing ability (ΔE (Hunter)) | 16.1 | 21.4 |
| Concealing ability evaluation | A | A |
| R450/R650 | 1.18 | 1.14 |
| Red-color transmitting property | D | D |
| Specific surface area m²/g | 5 | 6 |

*1: Tipaque CR-50 (manufactured by ISHIHARA SANGYO KAISHA, LTD., apparent average particle size: 200 nm, form: indefinite form)
*2: Bayer titanium A (manufactured by Bayer AG, apparent average particle size: 400 nm, form: indefinite form)

Both the rutile pigment grade titanium dioxide and the anatase pigment grade titanium dioxide were low in the red-color transmitting property. Even when these titanium oxides were calcined at high-temperature, the red-color transmitting properties were low.

The present inventors investigated on the possibility of producing a titanium dioxide excellent in concealing ability by using a rutile titanium dioxide having a high red-color transmitting property.

The present inventors used the method according to Patent Literature (Japanese Unexamined Patent Publication No. 2010-173863 A) and synthesized two kinds of titanium dioxide having different particle sizes and having needle-shaped projections on the particle surface where needle-shaped particles are radially oriented and aggregated.

The resultant titanium oxides were called as Titanium dioxide A (specific surface area: 101 m²/g, crystallite size: 5 nm, apparent average particle size: 0.2 to 0.3 μm, with needle-shaped projections) and Titanium dioxide B (specific surface area: 117 m²/g, crystallite size: 11 nm, apparent average particle size: 0.3 μm, with needle-shaped projections), respectively.

Titanium dioxide having needle-shaped projections on the particle surface where needle-shaped particles are radially orientated and aggregated which was commercially available (ST-730, manufactured by Titan Kogyo, Ltd.) was called as Titanium dioxide D (specific surface area: 98 m$^2$/g, crystallite size: 6 nm, apparent average particle size: 0.5 μm, with needle-shaped projections).

Titanium dioxide having needle-shaped projections on the particle surface where needle-shaped particles are radially orientated and aggregated which was commercially available (ST-750, manufactured by Titan Kogyo, Ltd.) was called as Titanium dioxide D (specific surface area: 84 m$^2$/g, crystallite size: 8.6 nm, apparent average particle size: 1.0 μm, with needle-shaped projections).

Titanium dioxide in which the particles are needle-shaped and which was commercially available (MT062, manufactured by Tayca Corporation) was called as Titanium dioxide E (specific surface area: 47 m$^2$/g, crystallite size: 23.3 nm, apparent average particle size: 65 nm, with needle-shaped projections).

Each titanium dioxide was used to produce a titanium dioxide powder by the following method. The produced titanium dioxide powder was evaluated by the above evaluation methods and was investigated on a relationship between a kind of titanium dioxide before the calcination and a calcination temperature. The results are shown in Tables 2 to 6.

(Production Method of Titanium Dioxide Powder)

100 g of titanium dioxide to be used as a mother nucleus was placed in a crucible made of quartz. Then, it was calcined at each temperature for 1 hour in a muffle furnace to produce a titanium dioxide powder.

Titanium dioxide A (specific surface area: 101 m$^2$/g, crystallite size: 5 nm, apparent average particle size: 0.2 to 0.3 μm, with needle-shaped projections)

TABLE 2

| Test example | 1-1 | 1-2 | 1-3 | 1-4 | 1-5 | 1-6 |
|---|---|---|---|---|---|---|
| Calcination temperature | 0 | 300 | 500 | 700 | 800 | 900 |
| Concealing ability (ΔE (Hunter)) | 33.9 | 26.2 | 22.7 | 19.9 | 18.3 | 17.6 |
| Concealing ability evaluation | C | C | B | A | A | A |
| R450/R650 | 1.58 | 1.45 | 1.43 | 1.42 | 1.29 | 1.14 |
| Red-color transmitting property evaluation | A | A | A | A | D | D |
| Ratio between minor axis and major axis | 1.4 | 1.4 | 1.4 | 1.4 | 1.3 | 1.3 |
| Specific surface area m$^2$/g | 101 | 62 | 32 | 14 | 13 | 5 |

Titanium dioxide B (specific surface area: 117 m$^2$/g, crystallite size: 11 nm, apparent average particle size: 0.3 μm, with needle-shaped projections)

TABLE 3

| Test example | 2-1 | 2-2 | 2-3 | 2-4 | 2-5 | 2-6 |
|---|---|---|---|---|---|---|
| Calcination temperature | 0 | 300 | 500 | 700 | 800 | 900 |
| Concealing ability (ΔE (Hunter)) | 34.0 | 25.2 | 21.7 | 18.8 | 16.8 | 17.2 |
| Concealing ability evaluation | C | C | A | A | A | A |
| R450/R650 | 1.57 | 1.48 | 1.42 | 1.40 | 1.31 | 1.19 |
| Red-color transmitting property evaluation | A | A | A | A | C | D |
| Ratio between minor axis and major axis | 1.4 | 1.4 | 1.4 | 1.4 | 1.3 | 1.3 |
| Specific surface area m$^2$/g | 117 | 68 | 30 | 18 | 15 | 6 |

Titanium dioxide C (specific surface area: 98 m$^2$/g, crystallite size: 6 nm, apparent average particle size: 0.5 μm, with needle-shaped projections)

TABLE 4

| Test example | 3-1 | 3-2 | 3-3 | 3-4 | 3-5 | 3-6 |
|---|---|---|---|---|---|---|
| Calcination temperature | 0 | 300 | 500 | 700 | 800 | 900 |
| Concealing ability (ΔE (Hunter)) | 34.8 | 25.9 | 23.2 | 19.6 | 19.3 | 19.1 |
| Concealing ability evaluation | C | C | B | A | A | A |
| R450/R650 | 1.45 | 1.33 | 1.31 | 1.19 | 1.13 | 1.09 |
| Red-color transmitting property evaluation | A | C | C | D | D | D |
| Ratio between minor axis and major axis | 1.3 | 1.3 | 1.3 | 1.3 | 1.3 | 1.3 |
| Specific surface area m$^2$/g | 98 | 56 | 27 | 10 | 9 | 6 |

Titanium dioxide D (specific surface area: 84 m²/g, crystallite size: 8.6 nm, apparent average particle size: 1.0 μm, with needle-shaped projections)

TABLE 5

|  | Test example | | | |
|---|---|---|---|---|
|  | 4-1 | 4-2 | 4-3 | 4-4 |
| Calcination temperature | 0 | 350 | 630 | 720 |
| Concealing ability (ΔE (Hunter)) | 49.5 | 47.6 | 45.2 | 44.6 |
| Concealing ability evaluation | C | C | C | C |
| R450/R650 | 0.9 | 0.9 | 0.9 | 0.9 |
| Red-color transmitting property evaluation | D | D | D | D |
| Ratio between minor axis and major axis | 1.3 | 1.3 | 1.3 | 1.2 |
| Specific surface area m²/g | 84 | 74 | 38 | 34 |

Titanium dioxide E (specific surface area: 47 m²/g, crystallite size: 23.3 nm, apparent average particle size: 65 nm, with needle-shaped projections)

TABLE 6

|  | Test example | | | |
|---|---|---|---|---|
|  | 5-1 | 5-2 | 5-3 | 5-4 |
| Form | needle-shaped | needle-shaped | needle-shaped | needle-shaped |
| Ratio between minor axis and major axis | 3.3 | 3.3 | 3.3 | 3.2 |
| Apparent particle size (nm) | 65 | 65 | 65 | 65 |
| Crystallite size (nm) | 23.3 | 23.3 | 24.3 | 26.9 |
| Specific surface area (m²/g) | 47 | 44 | 40 | 19 |
| Calcination temperature (° C.) | — | 350 | 630 | 720 |
| Red-color transmitting property | A | A | A | A |
| Concealing ability | C | C | C | C |

The concealing ability in Titanium oxides A to C was improved by increasing the calcination temperature. The specific surface area was decreased as the temperature rose, which tells that the voids existing in the particle were reduced by coagulation of the needle-shaped particles that were radially orientated and aggregated before the calcination. This led to an improvement of the apparent refractive index, and consequently, the concealing ability was improved. However, the red-color transmitting property was gradually deteriorated. In particular, when the calcination was performed at high temperature, sintering was caused excessively, and an initial red-color transmitting property was significantly deteriorated.

In particular, with respect to Titanium dioxide C having a large particle size, the red-color transmitting property was almost lost at 700° C. Titanium dioxide C.

With respect to Titanium dioxide D having needle-shaped particles radially orientated and aggregated like Titanium oxides A to C, the specific surface area was decreased as the temperature rose like in Titanium oxides A to C, but an improvement of the concealing ability was extremely small since it has significantly large apparent particle size. Furthermore, the red-color transmitting property was low before and after the calcination since it has significantly large apparent particle size: thus, the desired red-color transmitting property was not achieved.

With respect to Titanium dioxide E having a small article size before the calcination and is formed of a single needle-shaped particle, the shape did not change largely after the calcination and the red-color transmitting property was maintained, but the concealing ability did not improve at all.

Furthermore, titanium dioxide having different shapes were investigated.

Titanium dioxide of which the particles are granular which was commercially available (TTO55(A), manufactured by ISHIHARA SANGYO KAISHA, LTD.) was called as Titanium dioxide F (specific surface area: 37 m²/g, crystallite size: 24.8 nm, apparent average particle size: 50 nm, granular).

Titanium dioxide having rod-shaped particles orientated and aggregated in forms of straw bundles which was commercially available (ST643, manufactured by Titan Kogyo, Ltd.) was called as Titanium dioxide G (specific surface area: 132 m²/g, crystallite size: 8.6 nm, apparent average particle size: 200 nm, in form of straw bundles).

Titanium dioxide F (specific surface area: 37 m²/g, crystallite size: 24.8 nm, apparent average particle size: 50 nm, granular)

TABLE 7

|  | Test example | | | |
|---|---|---|---|---|
|  | 6-1 | 6-2 | 6-3 | 6-4 |
| Form | granular | granular | granular | granular |
| Ratio between minor axis and major axis | 1.7 | 1.7 | 1.7 | 1.7 |
| Apparent particle size | 50 | 50 | 50 | 50 |
| Crystallite size | 24.8 | 25.1 | 24.8 | 26.5 |
| Specific surface area | 37 | 38 | 32 | 35 |
| Calcination temperature | — | 350 | 630 | 720 |
| Red-color transmitting property | A | A | A | A |
| Concealing ability | C | C | C | C |

From Test Examples 6-1 to 6-4, it was found that when granular titanium dioxide is calcined at 350 to 720° C., the crystallite size does not change, and the specific surface area and the crystallite size do not become those of the calcined titanium dioxide of the present invention.

Accordingly, although the red-color transmitting property was achieved, the desired concealing ability was not achieved.

Titanium dioxide G (specific surface area: 132 m²/g, crystallite size: 8.6 nm, apparent average particle size: 200 nm, in form of straw bundles)

TABLE 8

|  | Test example | | | |
|---|---|---|---|---|
|  | 7-1 | 7-2 | 7-3 | 7-4 |
| Form | straw bundles | straw bundles | straw bundles | straw bundles |
| Ratio between minor axis and major axis | 2.5 | 2.5 | 2.5 | 2.5 |
| Apparent particle size | 200 | 200 | 200 | 200 |
| Crystallite size | 8.6 | 8.7 | 9.9 | 11.1 |
| Specific surface area | 132 | 79 | 34 | 39 |
| Calcination temperature | — | 350 | 630 | 720 |
| Red-color transmitting property | C | C | C | C |
| Concealing ability | C | B | B | B |

Like the titanium dioxide used as a mother nucleus in the present invention, the titanium dioxide used in Test Example 7-1 satisfies: (a) the apparent average particle size; (b) the average crystallite size measured by X-ray diffractometry; and (c) the specific surface area, but does not have needle-shaped projections on the particle surface. Moreover, sufficient red-color transmitting property and concealing ability cannot be achieved after the calcination since the ratio between the minor axis and the major axis is as large as 2.5.

From the above consideration, Titanium dioxide B having an acceptable temperature width in terms of improvement in the concealing ability and maintaining of the red-color transmitting property is suitable as titanium dioxide used as a mother nucleus in the present invention.

Figure 2:
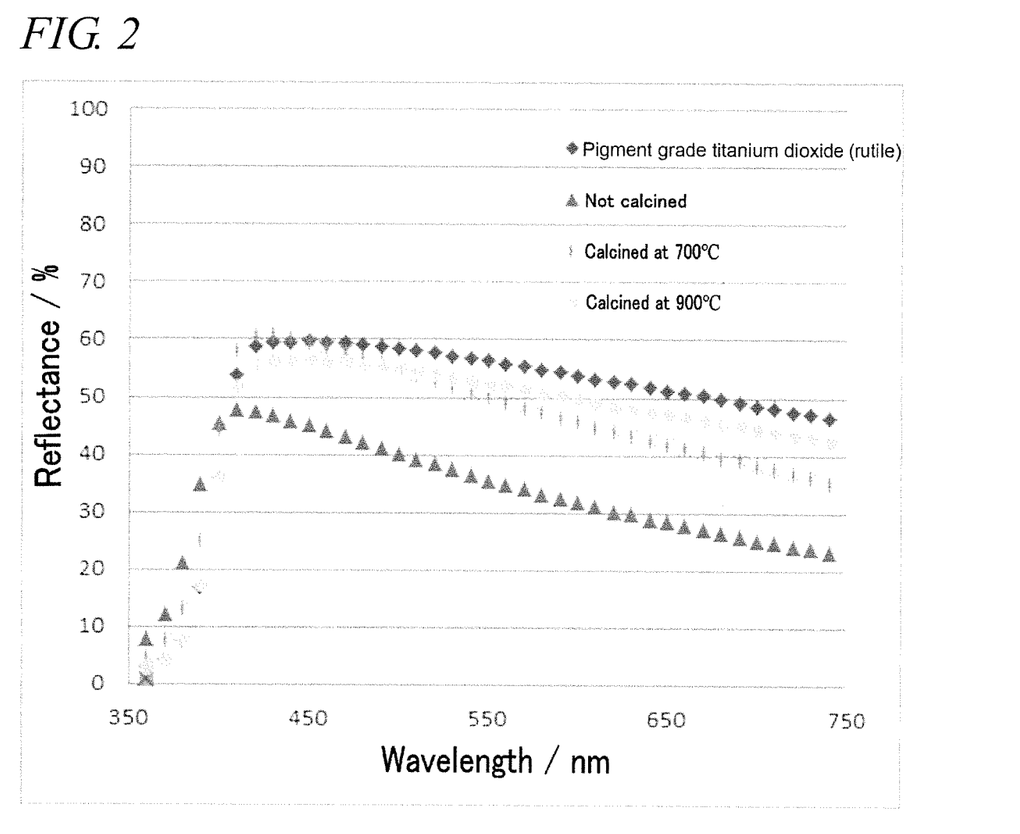
FIG. 2 shows the spectral reflectances of a rutile pigment grade titanium dioxide (*1), Titanium dioxide B (not calcined), and Titanium dioxide B calcined at 700 and 900° C.

Results of measurement of spectral reflectances of the rutile pigment grade titanium dioxide (*1) and Titanium dioxide B (not calcined, calcination temperature: 700° C., 900° C.) are shown in FIG. 2. The measurement was performed in such a manner that the titanium dioxide powder was dispersed and mixed into a nitrocellulose lacquer in a concentration of 5%, a resultant dispersion was applied to black and white concealing ability test charts in accordance with JIS-K5400 with a coating thickness of 0.101 μm and dried to prepare test samples, and using the prepared test samples, a colorimetric measurement was performed on each coating surface of a black portion of the charts with a spectrocolorimeter (CM-2600, manufactured by Konica Minolta, Inc.) to give the spectral reflectance.

Figure 3:
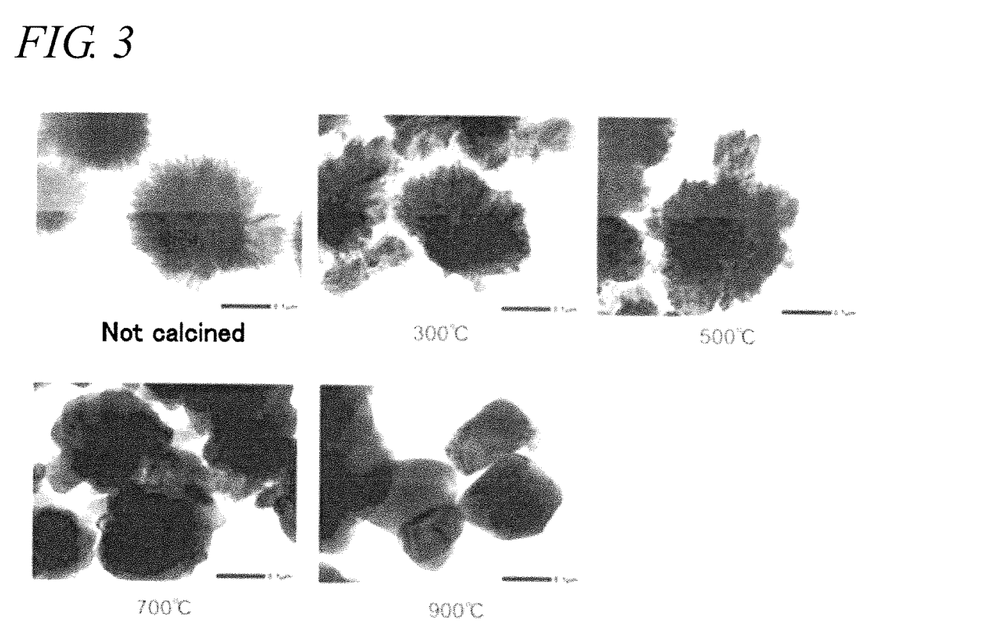
FIG. 3 is TEM observation showing a change in the shape of Titanium dioxide B at each calcination temperature.

With respect to Titanium dioxide B, TEM (transmission electron micrograph) images were taken before and after the calcination (calcination temperature: 300° C., 500° C., 700° C., 900° C.). The results are shown in FIG. 3.

Figure 4:
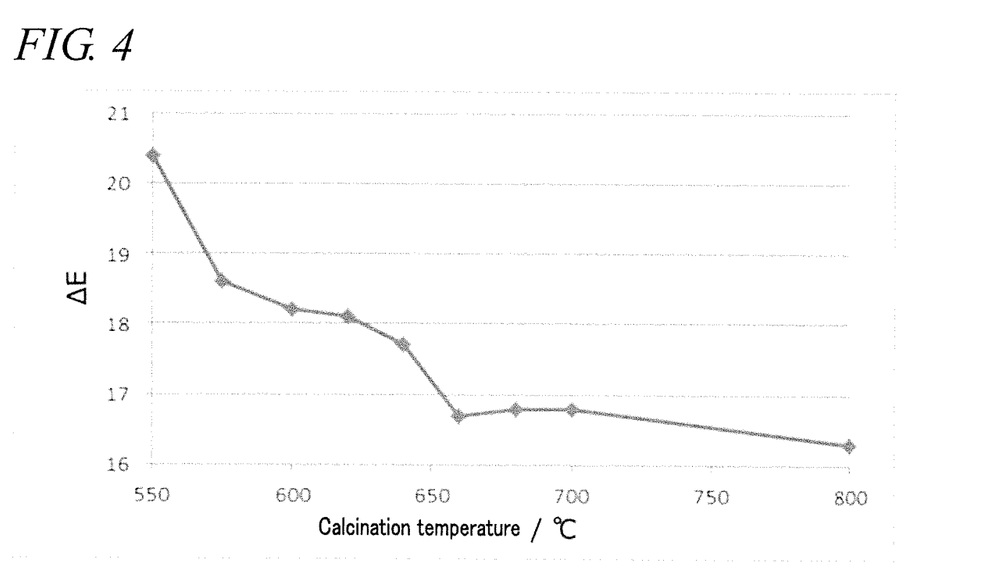
FIG. 4 shows a change in the concealing ability of Titanium dioxide B according to a change in the calcination temperature of a rotary kiln.
Figure 5:
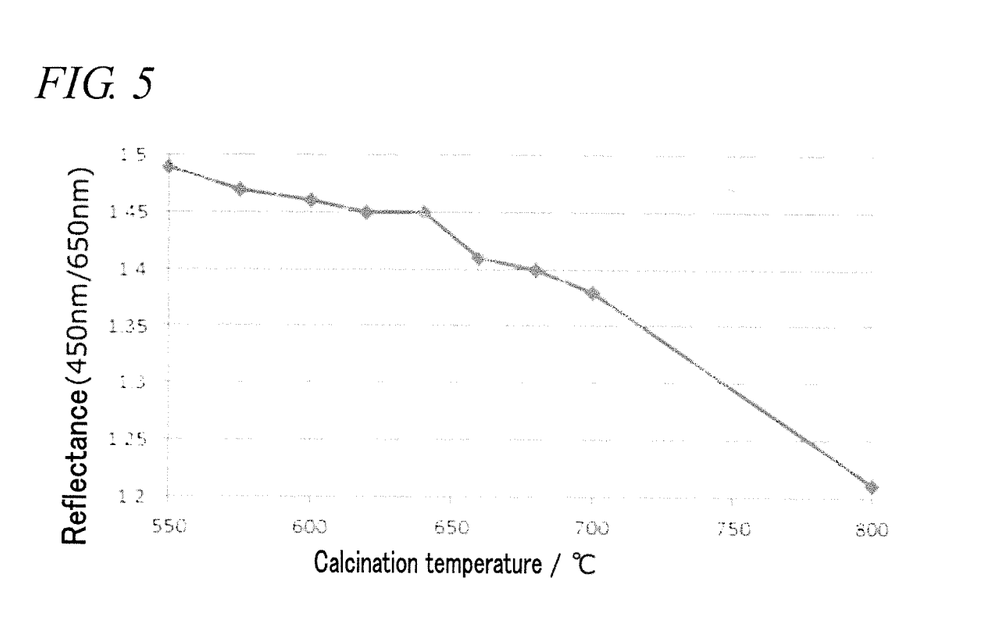
FIG. 5 shows a change in the red-light transmittance of Titanium dioxide B according to a change in the calcination temperature of a rotary kiln

Furthermore, the concealing ability and the red-color transmitting property according to changes in the calcination temperature were measured for Titanium dioxide B. The results are shown in FIG. 4 and FIG. 5, respectively.

Based on the above results, when the calcination is performed in the muffle furnace, an appropriate temperature range is from 500 to 800° C., and more desirably from 500 to 700° C.

Next, the present inventors investigated on the calcination temperature ranging from 500° C. to 800° C. in detail using Titanium dioxide B as a mother nucleus. That is, the present inventors evaluated a titanium dioxide powder calcined at various calcination temperatures by the above evaluation methods. The results are shown in Tables 5 and 6.

The calcination was performed in a rotary calcination furnace (rotary kiln) which allows a production close to a mass production with high calcination efficiency.

It is known that the rotary calcination furnace generally has a high calcination efficiency and can provide the same calcination state as the calcination performed in a static muffle furnace, with a lower temperature.

TABLE 9

| Calcination temperature | 0 | 550 | 575 | 600 | 620 | 640 |
|---|---|---|---|---|---|---|
| Ratio between minor axis and major axis | 1.4 | 1.4 | 1.4 | 1.4 | 1.4 | 1.4 |
| Average Crystallite size nm | 11 | 17 | 19 | 20 | 21 | 22 |
| Specific surface area | 117 | 21 | 20 | 18 | 18 | 17 |
| Concealing ability (ΔE (Hunter)) | 34.0 | 20.4 | 18.6 | 18.2 | 18.1 | 17.7 |
| Concealing ability evaluation | C | B | A | A | A | A |
| R450/R650 | 1.57 | 1.49 | 1.47 | 1.46 | 1.45 | 1.45 |
| Red-color transmitting property evaluation | A | A | A | A | A | A |

TABLE 10

| | Calcination temperature | | | |
|---|---|---|---|---|
| | 660 | 680 | 700 | 800 |
| Ratio between minor axis and major axis | 1.4 | 1.4 | 14 | 1.3 |
| Average Crystallite size nm | 24 | 27 | 29 | 33 |
| Specific surface area | 16 | 15 | 14 | 9 |
| Concealing ability (ΔE (Hunter)) | 16.7 | 16.8 | 16.8 | 16.3 |

TABLE 10-continued

| | Calcination temperature | | | |
|---|---|---|---|---|
| | 660 | 680 | 700 | 800 |
| Concealing ability evaluation | A | A | A | A |
| R450/R650 | 1.41 | 1.4 | 1.38 | 1.21 |
| Red-color transmitting property evaluation | A | B | B | D |

The specific surface area is an index that shows a reduction in voidage and a progression of the sintering of the obtained titanium dioxide particles. In the titanium dioxide used in the present invention, the specific surface area thereof becomes preferably within a range of 8 to 30% compared to that of before the calcination (100%) by calcining titanium dioxide powder used as a mother nucleus.

Based on these results, it was found that in order to obtain excellent concealing ability and red-color transmitting property, the calcination temperature is preferably 550 to 700° C., and more preferably 575 to 660° C.

[Emulsion Cosmetic]

Further, the present inventors used the titanium dioxide produced at the calcination temperature of 660° C. in Table 6 to prepare, in a usual manner, an emulsion cosmetic blended with a hydrophobized titanium dioxide produced by the surface treatment method below. The produced cosmetics were evaluated by the evaluation method below.

[Surface Treatment Method of Titanium Dioxide Powder]

The produced titanium dioxide powder was dispersed to ion-exchanged water, which was heated and then made to adsorb 3% by mass of n-Octyltriethoxysilane. Then, the resultant was dehydrated, washed, and dried to produce a surface-treated titanium dioxide.

[Production Method of Emulsion Cosmetic]

A powder phase comprising the above-mentioned surface treated titanium dioxide was mixed and dispersed to an oil phase, and an aqueous phase was added to emulsify.

[Evaluation Method of Emulsion Cosmetic]

Evaluation (6): Covering of Pigmented Spots and Freckles 10 trained-expert panelists applied the sample to their faces and evaluated feeling in use after application.

A: 9 or more out of 10 panelists answered that pigmented spots and freckles were covered.

B: 7 or more to less than 9 out of 10 panelists answered that pigmented spots and freckles were covered.

C: 5 or more to less than 7 out of 10 panelists answered that pigmented spots and freckles were covered.

D: less than 5 out of 10 panelists answered that pigmented spots and freckles were covered.

Evaluation (7): Unnoticeableness of Pores 10 trained-expert panelists applied the sample to their faces and evaluated feeling in use after application.

A: 9 or more out of 10 panelists answered that pores were unnoticeable.

B: 7 or more to less than 9 out of 10 panelists answered that pores were unnoticeable.
C: 5 or more to less than 7 out of 10 panelists answered that pores were unnoticeable.
D: less than 5 out of 10 panelists answered that pores were unnoticeable.

Evaluation (8): Natural Makeup Finish 10 trained-expert panelists applied the sample to their faces and evaluated feeling in use after application.
A: 9 or more out of 10 panelists answered that a makeup finish was natural.
B: 7 or more to less than 9 out of 10 panelists answered that a makeup finish was natural.
C: 5 or more to less than 7 out of 10 panelists answered that a makeup finish was natural.
D: less than 5 out of 10 panelists answered that a makeup finish was natural.

Evaluation (9): Non-Powdery Feeling 10 trained-expert panelists applied the sample to their faces and evaluated feeling in use after application.
A: 9 or more out of 10 panelists answered that a powdery feeling was not felt.
B: 7 or more to less than 9 out of 10 panelists answered that a powdery feeling was not felt.
C: 5 or more to less than 7 out of 10 panelists answered that a powdery feeling was not felt.
D: less than 5 out of 10 panelists answered that a powdery feeling was not felt.

Evaluation (10): Lightness in Spreadability 10 trained-expert panelists applied the sample to their faces and evaluated feeling in use after application.
A: 9 or more out of 10 panelists answered that spreading was light.
B: 7 or more to less than 9 out of 10 panelists answered that spreading was light.
C: 5 or more to less than 7 out of 10 panelists answered that spreading was light.
D: less than 5 out of 10 panelists answered that spreading was light.

Evaluation (11): Natural Redness 10 trained-expert panelists applied the sample to their faces and evaluated feeling in use after application.
A: 9 or more out of 10 panelists answered that a natural redness was obtained.
B: 7 or more to less than 9 out of 10 panelists answered that a natural redness was obtained.
C: 5 or more to less than 7 out of 10 panelists answered that a natural redness was obtained.
D: less than 5 out of 10 panelists answered that a natural redness was obtained.

TABLE 11

| Test Example | 8-1 | 8-2 | 8-3 | 8-4 | 8-5 | 8-6 | 8-7 | 8-8 |
|---|---|---|---|---|---|---|---|---|
| Cyclopentasiloxane | 40 | 40 | 40 | 40 | 40 | 40 | 40 | 40 |
| Isopropyl myristate | 3 | 3 | 3 | 3 | 3 | 3 | 3 | 3 |
| PEG-10 dimethicone | 2.5 | 2.5 | 2.5 | 2.5 | 2.5 | 2.5 | 2.5 | 2.5 |
| Glyceryl diisostearate | 1 | 1 | 1 | 1 | 1 | 1 | 1 | 1 |
| Dimethicone/vinyl dimethicone crosspolymer | 5 | 5 | 5 | 5 | 5 | 5 | 5 | — |
| Disteardimonium hectorite | 0.4 | 0.4 | 0.4 | 0.4 | 0.4 | 0.4 | 0.4 | 0.4 |
| Hydrophobized fine-particle titanium r | 8 | 8 | 8 | 8 | 8 | 8 | — | 8 |
| Nylon | — | — | — | — | — | — | 8 | 5 |
| Magnesium myristate-treated barium sulfate | 3 | 3 | 3 | 3 | 3 | 3 | 3 | 3 |
| Silicone-treated pigment grade titamiun dioxide | — | 8 | 6 | 8 | — | — | — | — |
| n-Octyltriethoxysilane titanium dioxide of the present invention calcined) | 8 | — | — | — | — | — | 8 | 8 |
| Hydrophobized spherical titanium dioxide | — | — | — | — | 8 | 10 | — | — |
| Silicone-treated colcothar | 0.35 | 0.35 | 0.35 | 0.42 | 0.35 | 0.35 | 0.35 | 0.35 |
| Silicone-treated yellow iron oxide | 1.1 | 1.1 | 1.1 | 1.1 | 1.1 | 1.1 | 1.1 | 1.1 |
| Silicone-treated black iron oxide | 0.05 | 0.05 | 0.05 | 0.05 | 0.05 | 0.05 | 0.05 | 0.05 |
| Ion-exchanged water | 20.6 | 20.6 | 22.6 | 20.53 | 20.6 | 18.6 | 20.6 | 20.6 |
| Dynamite glycerin | 3 | 3 | 3 | 3 | 3 | 3 | 3 | 3 |
| Alcohol 96 | 3.5 | 3.5 | 3.5 | 3.5 | 3.5 | 3.5 | 3.5 | 3.5 |
| Phenoxyethanol | 0.5 | 0.5 | 0.5 | 0.5 | 0.5 | 0.5 | 0.5 | 0.5 |
| Covering of pigmented spots and freckles | A | A | B | A | C | B | B | A |
| Unnoticeableness of pores | A | C | B | C | C | B | B | B |
| Natural makeup finish | A | C | B | C | B | B | A | A |
| Non-powdery feeling | A | D | B | D | B | C | A | A |
| Lightness in spreadability | B | B | B | B | B | D | B | B |
| Natural redness | A | C | C | C | B | B | A | A |

From Table 11, it was found that the emulsion cosmetic blended with titanium dioxide (calcined) of the present invention was excellent in feeling in use compared to the emulsion cosmetic blended with the hydrophobized spherical titanium dioxide.

The hydrophobized spherical titanium dioxide: particle size of 300 nm.

The hydrophobized fine-particle titanium dioxide: needle-shaped, minor axis of 0.005 to 0.05 μm, major axis of 0.01 to 0.02 μm.

Next, formulation examples of the present invention are shown below.

TABLE 12

| | Formulation example 1 |
|---|---|
| Cyclopentasiloxane | 40 |
| Isopropyl myristate | 3 |
| PEG-10 dimethicone | 2.5 |
| Polyglyceryl-2 diisostearate | 1 |
| PEG-15/lauryl polydimethylsiloxyethyl dimethicone crosspolymer | 5 |
| Disteardimonium hectorite | 0.4 |
| Hydrophobized fine-particle titanium dioxide | 8 |
| Magnesium myristate-treated barium sulfate | 3 |
| n-Octyltriethoxysilane titanium dioxide of the present invention (calcined) | 8 |
| Silicone-treated colcothar | 0.35 |
| Silicone-treated yellow iron oxide | 1.1 |
| Silicone-treated black iron oxide | 0.05 |
| Ion-exchanged water | To 100 |
| Dynamite glycerin | 3 |
| Alcohol 95% | 3.5 |
| Phenoxyethanol | 0.5 |
| Covering of pigmented spots and freckles | B |
| Unnoticeableness of pores | B |
| Natural makeup finish | A |
| Non-powdery feeling | B |

| Formulation Example 2: Liquid foundation | (% by mass) |
|---|---|
| Cyclopentasiloxane | 40 |
| Isopropyl myristate | 3 |
| PEG-10 dimethicone | 2.5 |
| Polyglyceryl-2 diisostearate | 1 |
| PEG-15/lauryl polydimethylsiloxyethyl dimethicone crosspolymer | 5 |
| Disteardimonium hectorite | 0.8 |
| Hydrophobized fine-particle titanium dioxide | 8 |
| n-Octyltriethoxysilane titanium dioxide of the present invention (calcined) | 2 |
| Silicone-treated colcothar | 0.35 |
| Silicone-treated yellow iron oxide | 1.1 |
| Silicone-treated black iron oxide | 0.05 |
| Ion-exchanged water | Balance |
| Dynamite glycerin | 3.5 |
| Ethanol | 3.5 |
| Phenoxyethanol | 0.5 |

| Formulation Example 3: Concealer | (% by mass) |
|---|---|
| Cyclopentasiloxane | 40 |
| Isopropyl myristate | 3 |
| PEG-10 dimethicone | 2.5 |
| Polyglyceryl-2 diisostearate | 1 |
| PEG-15/lauryl polydimethylsiloxyethyl dimethicone crosspolymer | 5 |
| Disteardimonium hectorite | 0.8 |
| Hydrophobized fine-particle titanium dioxide | 8 |
| n-Octyltriethoxysilane titanium dioxide of the present invention (calcined) | 25 |
| Silicone-treated colcothar | 0.35 |
| Silicone-treated yellow iron oxide | 1.1 |
| Silicone-treated black iron oxide | 0.05 |
| Ion-exchanged water | Balance |
| Dynamite glycerin | 15 |
| Ethanol | 3.5 |
| Phenoxyethanol | 0.5 |

| Formulation Example 4: Solid foundation | (% by mass) |
|---|---|
| Cyclopentasiloxane | 35 |
| Isopropyl myristate | 3 |
| PEG-10 dimethicone | 2.5 |
| Polyglyceryl-2 diisostearate | 1 |
| PEG-15/lauryl polydimethylsiloxyethyl dimethicone crosspolymer | 5 |
| Disteardimonium hectorite | 0.8 |
| Microcrystalline wax | 2 |
| Polyethylene wax | 3 |
| Hydrophobized fine-particle titanium dioxide | 8 |
| n-Octyltriethoxysilane titanium dioxide of the present invention (calcined) | 7 |
| Silicone-treated colcothar | 0.35 |
| Silicone-treated yellow iron oxide | 1.1 |
| Silicone-treated black iron oxide | 0.05 |
| Ion-exchanged water | Balance |
| Dynamite glycerin | 3.5 |
| Ethanol | 3.5 |
| Phenoxyethanol | 0.5 |

What is claimed is:

1. An emulsion cosmetic, comprising:
   0.1 to 25% by mass of said emulsion cosmetic of a titanium dioxide powder;
   0.1 to 5% by mass of said emulsion cosmetic of disteardimonium hectorite;
   0.1 to 8% by mass of said emulsion cosmetic of a silicone surfactant; and
   said titanium dioxide powder, further comprising:
      an apparent average particle size that is in a range of 100 to 500 nm;
      an average crystallite size that is in a range of 15 to 30 nm;
      a specific surface area that is in a range of 10 to 30 $m^2/g$; and
   wherein said titanium dioxide powder is a plurality of particles, each particle having needle-projections that are radially projected on a surface of said particle and coagulated, and a ratio between a minor axis and a major axis (major axis/minor axis) of said particle is in a range of 1.0 to 2.5;
   wherein said average crystallite size is measured by an X-ray diffractometry.

2. An emulsion cosmetic, comprising:
   0.1 to 25% by mass of said emulsion cosmetic of a rutile titanium dioxide powder;
   0.1 to 5% by mass of said emulsion cosmetic of disteardimonium hectorite;
   0.1 to 8% by mass of said emulsion cosmetic of a silicone surfactant; and
   said rutile titanium dioxide powder, further comprising:
      an average crystallite size that is in a range of 15 to 30 nm;
      a specific surface area that is in a range of 10 to 30 $m^2/g$;
      a reflectance at 450 nm that is 1.3 times larger or more than a reflectance at 650 nm m;

a color difference (ΔE) that is not more than 22; and
wherein said average crystallite size is measured using an X-ray diffractometry, and said color difference (ΔE) of said rutile titanium dioxide powder is obtained using a method comprising steps of:
dispersing and mixing said rutile titanium dioxide powder in a nitrocellulose lacquer to make a 5% concentration;
applying an obtained dispersion to make a coating having a thickness of 0.101 μm on a black-and-white concealing level test chart, JIS-K5400;
drying to prepare a test sample;
measuring a color of each coating surface of a white paper and a black paper of said test sample using a spectrocolorimeter; and
calculating said color difference (ΔE) based on a Hunter Lab color space.

3. An emulsion cosmetic, comprising:
0.1 to 25% by mass of said emulsion cosmetic of a titanium dioxide powder;
0.1 to 5% by mass of said emulsion cosmetic of disteardimonium hectorite;
0.1 to 8% by mass of said emulsion cosmetic of a silicone surfactant; and
said titanium dioxide powder, further comprising:
an apparent average particle size that is in a range of 100 to 500 nm;
an average crystallite size that is in a range of 15 to 30 nm;
a specific surface area that is in a range of 10 to 30 $m^2/g$; and
wherein said titanium dioxide powder is a calcined second rutile titanium dioxide powder that is obtained by calcinating a first rutile titanium dioxide, said first rutile titanium dioxide having needle particles radially orientated and aggregated and needle projections on a particle surface thereof and further comprising:
(a) an apparent-average particle size that is not less than 100 nm and less than 500 nm;
(b) an average crystallite size that is in a range of 1 to 25 nm;
(c) a specific surface area that is in a range of 40 to 200 $m^2/g$; and
wherein said average crystallite size is measured by an X-ray diffractometry.

4. An emulsion cosmetic, comprising:
0.1 to 25% by mass of said emulsion cosmetic of a titanium dioxide powder;
0.1 to 5% by mass of said emulsion cosmetic of disteardimonium hectorite;
0.1 to 8% by mass of said emulsion cosmetic of a silicone surfactant, and
wherein said titanium dioxide powder is a calcined second rutile titanium dioxide powder that is obtained by calcinating a first rutile titanium dioxide having needle projections on a particle surface thereof and further comprising:
(a) an apparent-average particle size that is not less than 100 nm and less than 500 nm;
(b) an average crystallite size in a range of 1 to 25 nm;
(c) a specific surface area in a range of 40 to 200 $m^2/g$; and
wherein said specific surface area of said calcined second rutile titanium dioxide powder is in a range of 8 to 50% of a specific surface area of said first rutile titanium dioxide, and said average crystallite size is measured using an X-ray diffractometry.

5. The emulsion cosmetic, according to claim 3, wherein:
a calcination temperature for said first titanium dioxide is in a range of 500 to 700° C.

6. The emulsion cosmetic, according to claim 5, wherein:
said calcination temperature for said first titanium dioxide is in a range of 600 to 700° C.

7. The emulsion cosmetic, according to claim 1, wherein:
a reflectance of said titanium dioxide powder at 450 nm is 1.3 times larger or more than a reflectance of said titanium dioxide powder at 650 nm.

* * * * *